US008773151B2

(12) United States Patent
Min et al.

(10) Patent No.: US 8,773,151 B2
(45) Date of Patent: Jul. 8, 2014

(54) METHOD AND DEVICE FOR MULTICHANNEL MULTIFREQUENCY ANALYSIS OF AN OBJECT

(75) Inventors: Mart Min, Tallinn (EE); Paul Annus, Tallinn (EE); Alar Kuusik, Tallinn (EE); Raul Land, Tallinn (EE); Toomas Parve, Tallinn (EE); Ants Ronk, Tallinn (EE); Antti Haapalainen, Helsinki (FI)

(73) Assignee: OÜ Eliko Tehnoloogia Arenduskeskus, Tallinn (EE)

( * ) Notice: Subject to any disclaimer, the term of this patent is extended or adjusted under 35 U.S.C. 154(b) by 1503 days.

(21) Appl. No.: 12/298,389

(22) PCT Filed: Apr. 24, 2007

(86) PCT No.: PCT/EE2007/000007
§ 371 (c)(1),
(2), (4) Date: May 26, 2010

(87) PCT Pub. No.: WO2007/121756
PCT Pub. Date: Nov. 1, 2007

(65) Prior Publication Data
US 2010/0225303 A1    Sep. 9, 2010

Related U.S. Application Data

(60) Provisional application No. 60/745,488, filed on Apr. 24, 2006.

(51) Int. Cl.
*G01R 27/08*  (2006.01)
(52) U.S. Cl.
USPC .................. 324/707; 324/709; 324/76.24

(58) Field of Classification Search
USPC ..................... 324/707, 709, 76.24
See application file for complete search history.

(56) References Cited

U.S. PATENT DOCUMENTS

| 4,800,885 | A |   | 1/1989  | Johnson |
|-----------|---|---|---------|---------|
| 5,182,513 | A | * | 1/1993  | Young et al. .................. 324/232 |
| 5,272,624 | A |   | 12/1993 | Gisser et al. |
| 5,482,041 | A | * | 1/1996  | Wilk et al. .................... 600/430 |
| 5,892,746 | A | * | 4/1999  | Heo et al. ..................... 369/59.25 |

(Continued)

FOREIGN PATENT DOCUMENTS

| DE | 19911325 C1    | 7/2000 |
| WO | 2005109700 A   | 11/2005 |
| WO | 2005/122889 A1 | 12/2005 |

OTHER PUBLICATIONS

PCT Search Report dated Jun. 23, 2008 of Patent Application No. PCT/EE2007/000007 filed Apr. 24, 2007.

(Continued)

*Primary Examiner* — Jeff Natalini
(74) *Attorney, Agent, or Firm* — Maine Cernota & Rardin

(57) ABSTRACT

A method for multichannel multifrequency analysis of an object, applying a set of excitation signals to the object and sampling the response signal from the object, using uniform and non-uniform undersampling. Non-uniform sampling of the response signal is performed, i.e., the sampling is performed for two or more different frequencies in one observation time slot. Also, uniform sampling of the response signal is performed, i.e., the sampling of a signal, corresponding to one frequency, is performed for two or more channels within one observation time slot and then sampling the same signal for another frequency for two or more channels within the next observation time slot.

17 Claims, 8 Drawing Sheets

(56) References Cited

U.S. PATENT DOCUMENTS

| | | |
|---|---|---|
| 6,262,563 B1 | 7/2001 | Champlin |
| 6,462,787 B1 * | 10/2002 | Zohar et al. ................... 348/614 |
| 7,030,627 B1 | 4/2006 | Ashley |
| 2005/0021254 A1 | 1/2005 | Merl et al. |
| 2005/0283091 A1 | 12/2005 | Kink et al. |
| 2007/0043303 A1 * | 2/2007 | Osypka et al. ................ 600/547 |

OTHER PUBLICATIONS

Dudykevych, T. et al., "Impedance Analyser Module for EIT and Spectroscopy Using Undersampling", Physiological Measurement, 2001, pp. 19-24, vol. 22.

* cited by examiner

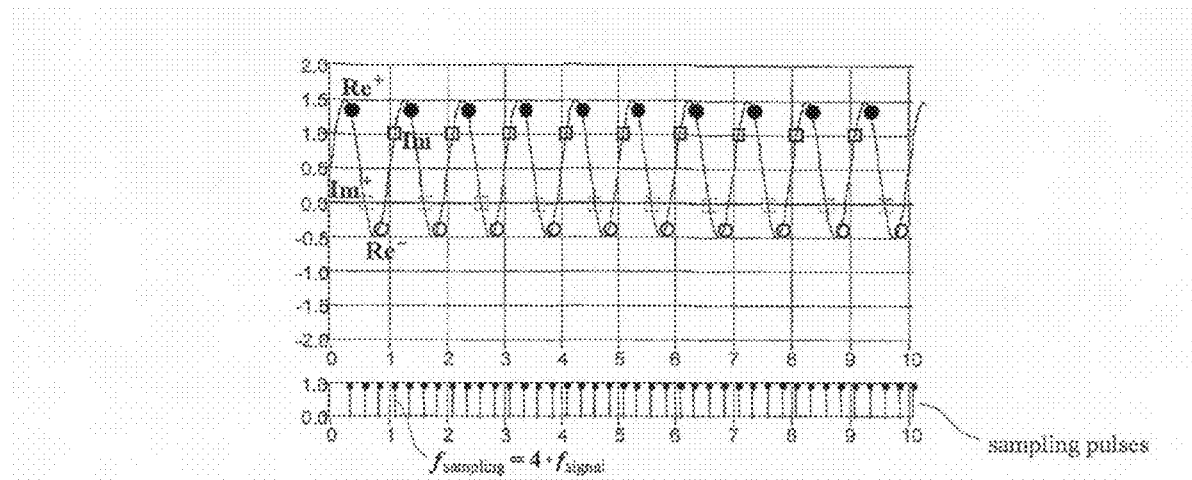
FIG. 4
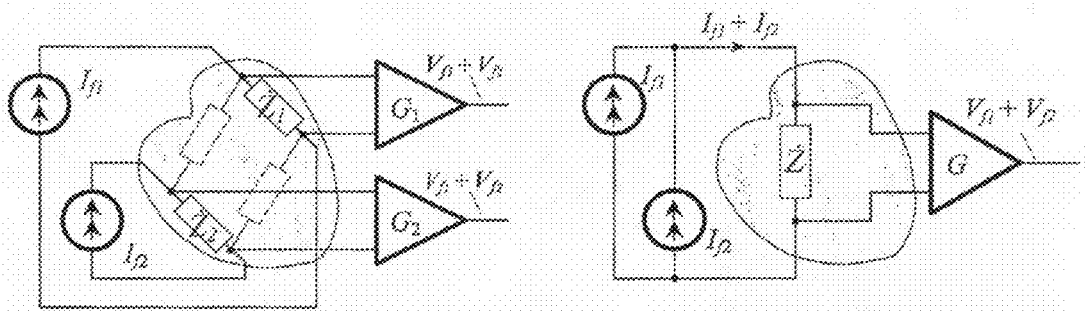 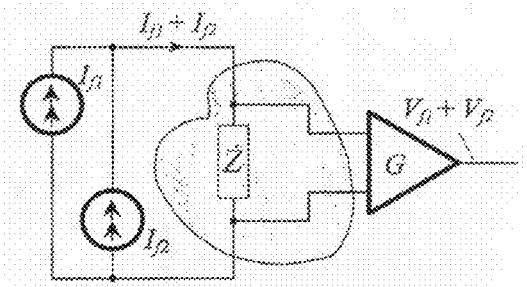
FIG. 5  FIG. 6
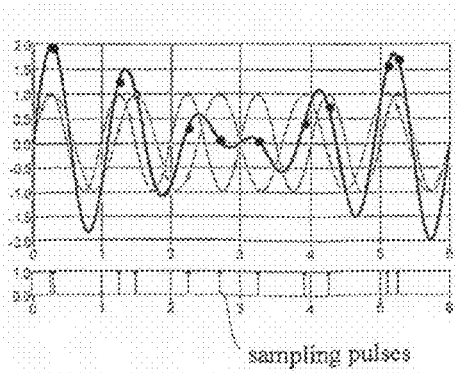 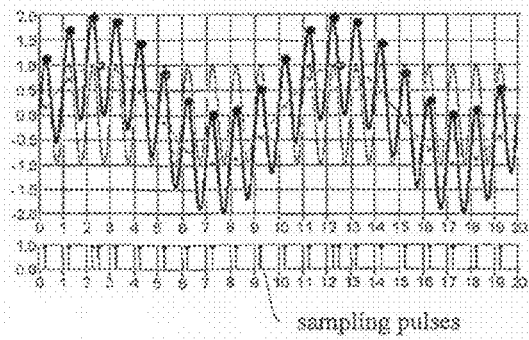
FIG. 7  FIG. 8

METHOD AND DEVICE FOR MULTICHANNEL MULTIFREQUENCY ANALYSIS OF AN OBJECT

RELATED APPLICATIONS

This application claims priority to PCT Application No. PCT/EE2007/000007, filed Apr. 24, 2007, which claims the benefit of U.S. Provisional Patent Application No 60/745, 488, filed Apr. 24, 2006. This application is also related to PCT application PCT/EE2005/000008, filed Jun. 20, 2005, and designating the United States of America (published as WO20051122889 on Dec. 29, 2005). All of these applications are incorporated herein by reference—in their entirety for all purposes.

TECHNICAL FIELD

The invention relates to the field of methods and devices for multichannel and multifrequency measurement of objects, such as chemical substances (e.g., solutions) and biological substances (e.g., tissues), and systems (e.g., amplifiers, filters). The method is particularly useful for measuring and monitoring of electrical bioimpedance of biological substances.

BACKGROUND OF THE INVENTION

Biomedical Background

Measurement of electrical bioimpedance enables to characterize a state of tissues/organs, to get diagnostic images, to find hemodynamical parameters, etc.

An excitation current is applied to the tissue under the study and a voltage response is measured. There are two different current paths through the tissue, the first one proceeds through the extracellular fluid and has a resistive character, and the other (intracellular) passes through the cell membranes and thus, has a capacitive character. The electrical bioimpedance $\dot{Z}=V/I_{exc}$ can be expressed as a complex parameter:

$$\dot{Z}=R+jX=Z\cdot e^{j\Phi},$$

with a real part R and an imaginary (capacitive) part X, or a magnitude Z and a phase $\Phi$.

Bioimpedance measurement has number of applications, including in cardiography, e.g., noninvasive plethysmography, multielectrode invasive estimation of the ventricular volume, intracardiac impedance based pacing control, and biomodulation measurements (see also FIGS. 1 to 3).

Engineering Background

As a rule, parameterization of different compartments of a tissue or an organ is required. Therefore, the impedance of tissues and organs is measured between electrodes having different location. The time domain variation of impedances can differ significantly at different sites. Also variations of impedance at distant low and high ($\omega_L$ and $\omega_H$) excitation frequencies can be quite different. The frequency dependence can be explained by $\dot{Z}(\omega_L)$ and $\dot{Z}(\omega_H)$ of the three element electrical equivalent.

Analog synchronous demodulation (SD) has been a preferred tool for electrical bioimpedance (EBI) measurement for many decades already, especially in portable, wearable and implantable medical devices. However, with advancements of microelectronics, a shift from analog signal processing towards digital has become more and more justified. Digital solutions allow reduction in size, reduce energy consumption, complexity and price. Also, digital techniques can enhance reliability trough redundancy in mission critical medical devices. Also, the flexibility of digital systems through their programmability will decide in favor of digital solutions.

According to typical digital solution, the response voltage is digitized in an analog-to-digital converter (ADC) into a uniformly sampled train of digital data, which is then processed numerically in a digital signal processing (DSP) unit, often using the Discrete Fourier Transform (DFT). However, transforming the time domain processes into frequency domain and applying then FFT for frequency domain extraction to different frequency components from the composite response signal, and applying the inverse FFT for getting back the time domain processes, is a complicated digital processing which requires powerful processors for performing it in real time and fulfilling the Nyquist criterion (sampling rate must be at least two to five time of the frequency of the signal component).

Required, therefore, is an approach that requires less computational power using undersampling (sampling rate lower than the Nyquist rate).

Using of sampling, which is synchronous to the known excitation waveform enables to use a simplified, but much faster signal processing than Fourier Transform is. When sampling the response signal uniformly with intervals $\tau=T/4$ (see FIG. 4), where T is a period of the signal, the following simple mathematics is valid:

the direct current component DC can be determined as $$DC=(Re^++Re^-)/2 \text{ or } DC=(Im^++Im^-)/2,$$

and the real Re and imaginary Im parts of the phasor $\dot{Z}$ of complex impedance is determined as $$Re=(Re^+-Re^-)/2, \text{ and } Im=(Im^+-Im^-)/2.$$

If the frequency of excitation signal is too high compared to the speed of analog to digital converter, or the power resources are limited, it is reasonable to use undersampling, keeping an exact synchronization between the excitation and sampling (see T. Dudykevych, E. Gersing, F. Thiel and G. Hellige, "Impedance Analyser Module for EIT and Spectroscopy Using Undersampling", *Physiological Measurement*, No. 22, Institute of Physics Publ. Ltd, UK, pp. 19-24, 2001; U.S. provisional application 60/580,831 and PCT/EE2005/000008 to Min et al).

When examining body parts or organs (thorax, heart, myocardium, lungs etc), only a single frequency excitation cannot give sufficient information about the bio-object. At least the two-frequency measurement is necessary according to the simple two-element equivalent circuit. The measurements at several frequencies must be performed simultaneously to follow the dynamic behavior of the changing bio-object properly (see above patent applications to Min).

For example, a digital multichannel bioimpedance analyzer must perform simultaneous measurement of complex bioimpedances (between the electrodes put into the heart) at eight frequencies from 1 or 10 kHz up to 1 MHz. The sinusoidal excitation currents of these frequencies must be sent to (K=1, 2 or 4) excitation electrodes and the summary response voltages must be measured at (up to) four measurement electrodes. Every response is a sum of eight excitations modulated by slowly varying bioimpedances (which include heartbeat and breathing components) and a slowly varying offset (caused by bioelectrical activity of the heart).

Proposed, therefore, are algorithms to measure the electrical bioimpedance, using numerical synchronous detection.

One suggestion is to extend synchronous sampling to the multifrequency measurement. Several, only slightly different frequencies are used instead of a single frequency excitation when different impedances of the organ are measured simultaneously (FIG. 5) or a single impedance at different frequencies (FIG. 6). However, the non-uniform nature of the resulting sampling pattern should be noted in this case (FIGS. 7 and 8). For example, when considering impedance cardiography (ICG) or similar applications, responses from several points are required to receive simultaneously together with the need to simultaneous multipoint excitation. It can be achieved using several slightly different excitation frequencies. Of course, this frequency differences must be small enough to enable the same or close to the same, results.

However, the above method has limitations. First, the choice of excitation must be such that a measurement interval (observation time slot) contains an integer number of periods of all the signals to be measured. Also, some samples (as the first samples for different but still close frequencies) must be taken closer in time than the time interval required by analog-to-digital converters (ADC) to perform each conversion. One workaround to the problem would be using several ADCs in parallel, but it will result in increased cost and excessive complexity.

Further complications arise when multiple channels should be digitized simultaneously, as it is typical when mapping of the 3D distribution of impedance variations. For n excitation sine waves and m measurement inputs the number of ADC's would be m times n, which is clearly not feasible.

Therefore, there is a need for yet another alternative approach.

SUMMARY OF THE INVENTIONS

One aspect of the invention is new signal processing method for determining complex impedance, based on Fourier transformation, using undersampling and sparsity of the excitation/response spectrum.

Another aspect of the invention is new signal processing method for determining complex impedance, based on digital synchronous detection, using undersampling and sparsity of the excitation/response spectrum.

Another aspect of the invention is a method for multichannel multifrequency analysis of an object, where synchronous uniform sampling is used, comprising generating at least one set of excitation signals, comprising components with predetermined frequencies, and corresponding at least one set of phase related sampling instances for at least one observation slot, applying said set of excitations signals to the object, receiving at least one modulated multicomponent response signal from the object and, and demodulating said multicomponent response signal by quantizing and processing to introducing excitation signal with said set of phase related sampling instances, wherein the quantizing is performed for each frequency of interest of said response signal in predetermined mode and obtaining a set of main frequency and time tagged estimates, each of said estimates comprising a plurality of sub-estimates, said sub-estimates representing a signal value, taken for said observation time slot.

According to one aspect of the invention, the non-uniform sampling of the response signal is performed, i.e., the sampling is performed for two or more different frequencies in one observation time slot.

According to another aspect of the invention, uniform sampling of the response signal is to performed, i.e., the sampling of a signal, corresponding to one frequency, is performed for two or more channels within one observation time slot and then sampling the same signal for another frequency for two or more channels within the next observation time slot.

Another aspect of the invention is a method for providing higher analog to digital conversion rate at required speed by converting a first analog signal in first analog to digital converter to a first digital signal, inverting the first digital signal, converting the first digital signal into a second analog signal, using digital to analog converter, summing the first analog signal and the second analog signal, amplifying the resulting signal by a factor, corresponding to a required number of bits, and converting the amplified signal into a second digital signal in a second analog to digital converter.

For example, amplifying the resulting signal 128 times corresponds to 7 bits ($2^7$).

The features and advantages described herein are not all-inclusive and, in particular, many additional features and advantages will be apparent to one of ordinary skill in the art in view of the drawings, specification, and claims. Moreover, it should be noted that the language used in the specification has been principally selected for readability and instructional purposed, and not to limit the scope of the inventive subject matter.

BRIEF DESCRIPTION OF THE DRAWINGS

FIG. 1: noninvasive plethysmography,

FIG. 2: multielectrode invasive estimation of the ventricular volume,

FIG. 3: intracardiac impedance based pacing control.

FIG. 4 depicts synchronous sampling of a single wave response (sampling frequency is 4 times the frequency of the response signal)

FIG. 5 to FIG. 8 depict simultaneous measurement of responses from the object with electrical bioimpedance Z to two excitation signals, whereas in FIG. 5 the excitation signals have slightly different frequencies $f_1$ and $f_2$, that are applied to two different locations of the object, and FIG. 7 depicts the response signal to these two excitation signals and using non uniform synchronous sampling to separate responses to different excitation signals, and in FIG. 6, the excitation signals have different frequencies $f_1$ and $f_2$, that are applied to the same location of the object, and FIG. 8 depicts the response signal to these two excitation signals and using non uniform synchronous sampling to separate responses to different excitation signals

Figure 13:
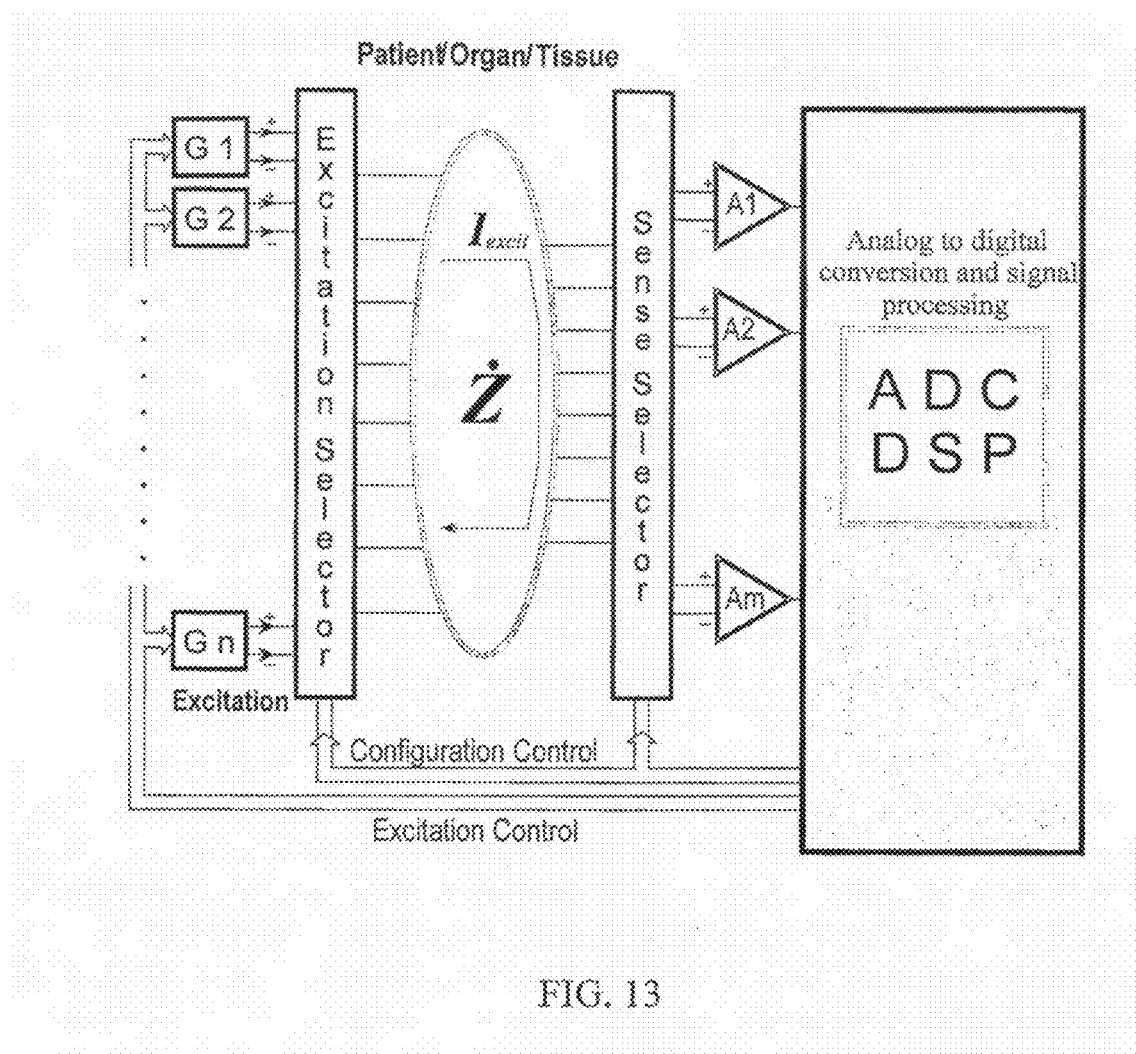
FIG. 13 depicts an architecture of the electrical bioimpendance measurement set-up, where multiple channels should be digitized simultaneously, e.g., for mapping the 3D distribution of impedance variations (for n excitation sine waves and m measurement inputs, m times n simultaneous analog to digital conversions are required)

DETAILED DESCRIPTION OF THE INVENTIONS is Architecture of a multichannel multifrequency electrical bioimpedance measurement set-up is depicted in FIG. 13. Sine wave signals from n generators G1 to Gn are selectively applied through the excitation selector to the object through one to n excitation electrodes. m measurement electrodes are selectively connected through the sense selector to the analog-to-digital conversion and digital signal processing. For example, signals with 8 different frequencies from 1 (or 10) kHz up to 1 MHz may be sent to 1 to 4 excitation electrodes and the response voltages are measured up to four measurement electrodes.

According to a traditional approach using analog to digital conversion, it would require n time m analog to digital converters for n excitation signal waves and m measurement inputs that is clearly not feasible.

Figure 10:
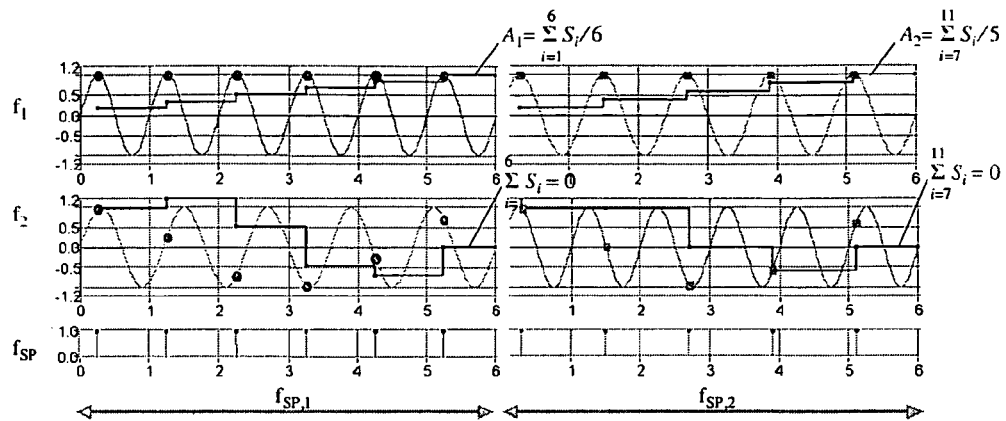
FIG. 10 illustrates the method of piecewise uniform sampling of response signal to two excitation signals with slightly different frequencies ($f_1/f_2$ equals 6/5) within two sequential observation slots with equal lengths (t equals $6/f_1$), and corresponding uniform trains of sampling pulses for each observation slots.

One way to approach the problem is to use non uniform synchronous sampling as described in U.S. provisional application 60/580,831, filed Jun. 18, 2004, and in PCT application PCT/EE2005/000008. According to this method, several, only slightly different frequencies (see, for example, frequencies $f_1$ and $f_2$ in FIGS. 10, and 12—note that the method is also applicable for more than 2 frequencies, e.g., for 8 frequencies) are used instead of a single frequency excitation when different impedances of the organ are measured simultaneously (FIG. 5). However, the non-uniform nature of the resulting sampling pattern should be noted in this case (FIG. 7). For example, when considering impedance cardiography (ICG) or similar applications, responses from several points are required to receive simultaneously together with the need to simultaneous multipoint excitation. It can be achieved using several slightly different excitation frequencies. Of course, this frequency differences must be small enough (approximately 10%) to enable the same or close to the same, results.

Figure 1:
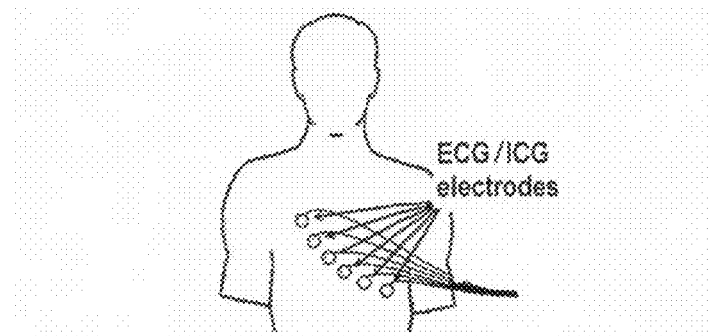
FIGS. 1 to 3 depict several cardiographical applications of electrical bioimpedance measurement.
Figure 2:
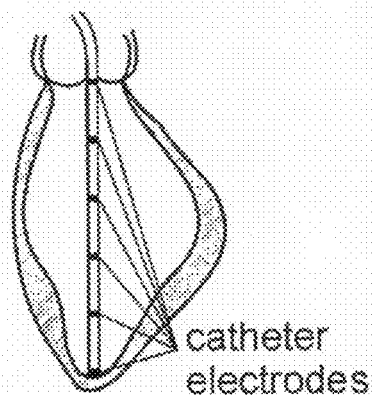
Figure 3:
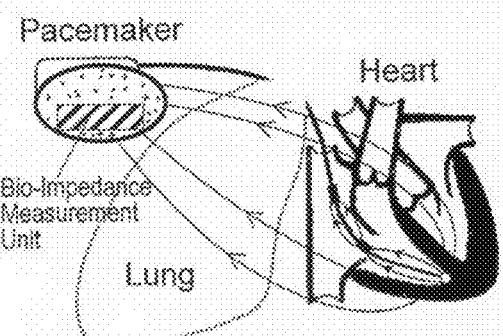
Figure 9:
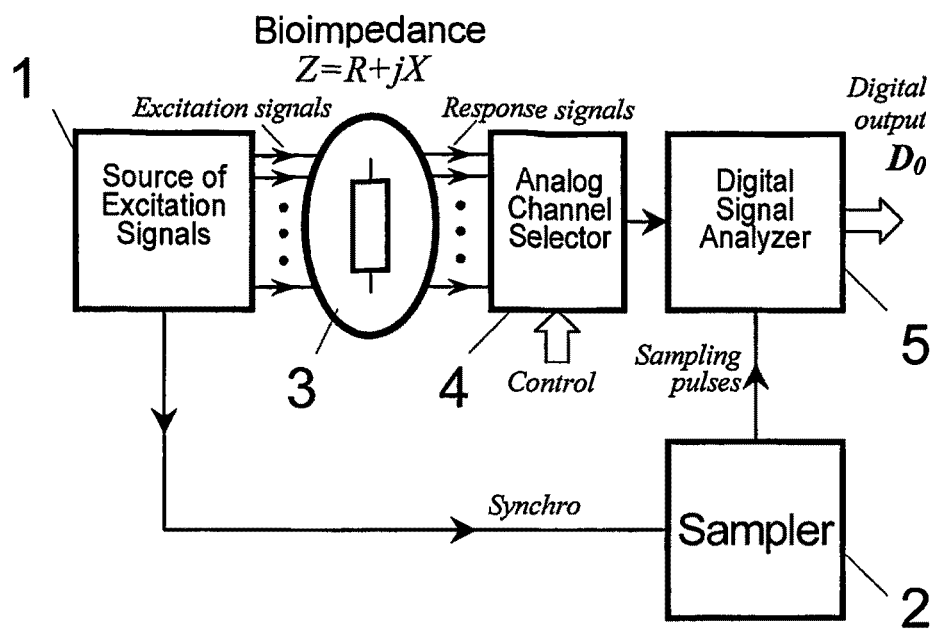
FIG. 9 depicts a block diagram of one device that can be used to generate and measure signals according to FIGS. 5 to 8.

However, this approach also has certain limitations. It is not possible to choose arbitrary excitation frequencies due to the special sampling algorithm: a measurement interval (also called observation time slot) must contain integer number of periods of all the signals with different frequencies to be measured. The strict requirements to speed of sampling circuits limits application possibilities. In FIG. 7, 6 cycles of $f_1$ and 5 cycles of $f_2$ are used, whereas $f_1/f_2=6/5$. As shown in FIG. 7, the two first samples are so close that they are practically coinciding. Analog-to-digital converters (ADC) do not allow sampling with arbitrary small time distances between two adjacent samples, because a certain time is required for every conversion. The problem can be reduced by using several ADCs in parallel, whereas distances between the samples are then limited only with system master clock period. However, this increases the complexity and the cost of the device. As already mentioned, further complications arise when multiple channels should be digitized simultaneously (see FIGS. 7 and 8) as it is typical when mapping of the 3D distribution of impedance variations is required (see FIGS. 1 to 2).

Figure 12:
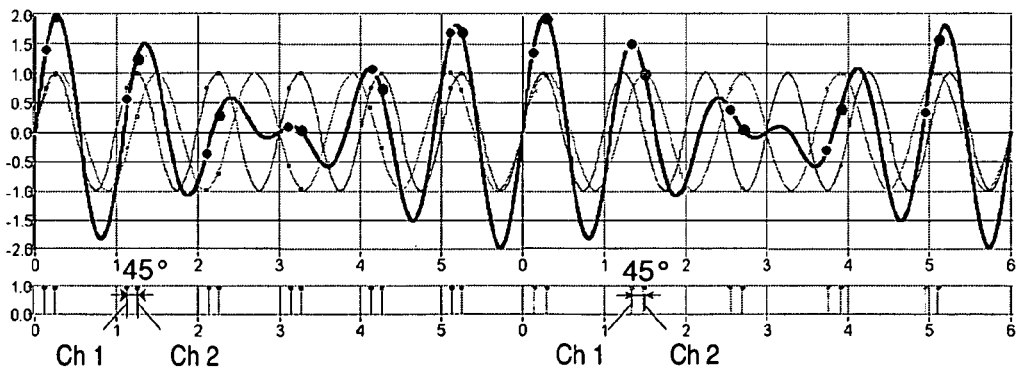
FIG. 12 further illustrates the method of FIG. 10, showing the sampling moments for two input channels and two frequencies in each, whereas first response to $f_1$ is sampled for both channels in the first observation slot and then $f_2$ is sampled for both channels in the second observation slot.

One possible solution is to rearrange samples in a time multiplexed manner. Measurements from several excitation electrodes with a single analog to digital converter can be done sequentially in time by multiplexing the inputs. Every input signal from each electrode contains responses to all the excitations with different frequencies. Instead of measuring of all the response signals from one channel (within one observation time slot) and then switching over to the next (as described above), the proposed solution does it in opposite order. First, the sampling of one frequency component from all the inputs takes place by introducing deliberate phase shift with fast multiplexing (see first observation slot $f_{sp,1}$ in FIG. 10), and then taking the next frequency component for sampling (see second observation slot $f_{sp,2}$ in FIG. 10). As a result, uniform sampling can be used. It means that for two channels and uniform spacing between the channel samples one of the signals will be sampled off the phase by −45° (FIG. 12). It can be handled as turning of the co-ordinate system (ReŻ and ImŻ axes) by 45 degrees.

Figure 11:
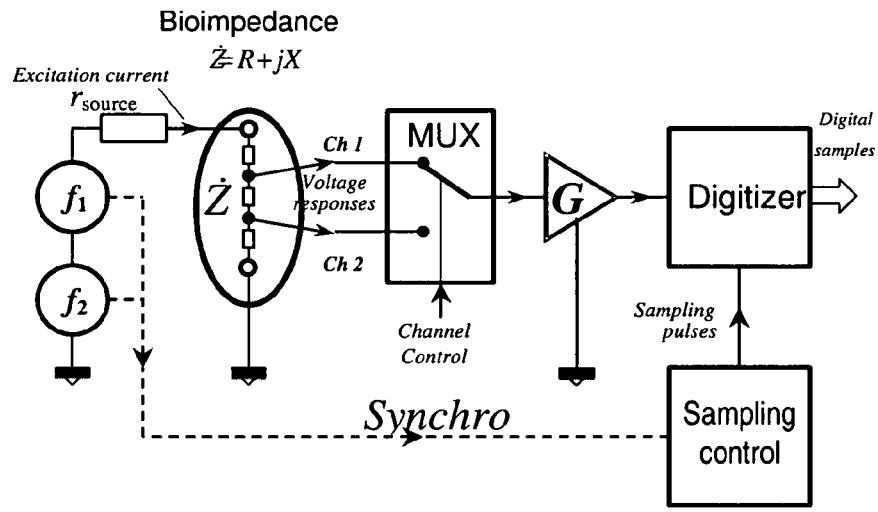
FIG. 11 illustrates a block diagram of one embodiment of a device, suitable for time division mode measurement with channel multiplexing according to FIG. 10.

Device as depicted in FIG. 11, uses this approach. Excitation current with comprising components with frequencies $f_1$ and $f_2$ is introduced into the object through excitation electrodes. Response signals are connected through multiplexer MUX and gain amplifier G to the digitizer, where the response signals from two channels to two frequencies $f_1$ and $f_2$ are digitized, using uniform synchronous sampling. Both channel control and sampling control must be synchronized.

In general, for the m input channels and n excitations, the phase shift for a channel k=1 . . . m will be 90[(1−k)/m] degrees (see FIG. 12). Such a phase shift is constant and can be taken into account easily when interpreting measurement results. It is easy to see that in contrast to the original solution, the proposed solution will not require non-uniform sampling during measurement of one frequency component in all the channels. Practical measurement on body surface (thorax EBI measurements) with 8 excitation sources and also 8 response signals require to operate in the frequency range of interest between 30 kHz and 100 kHz. The task can be accomplished using a single ADC with at least 10 MHz sampling rate. The resolution at least 18 to 20 bits is required to represent low (0.01% range) impedance changes adequately.

Figure 14:
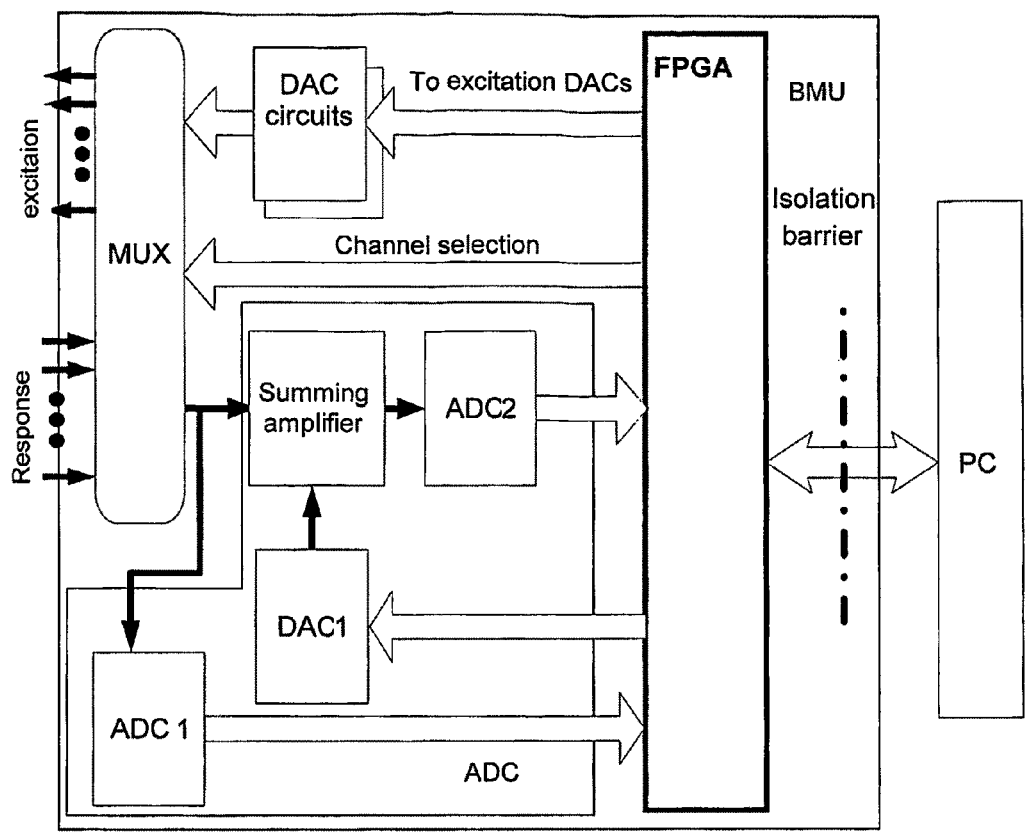
FIG. 14 is a functional diagram of a bioimpedance measurement unit (BMU), designed to implement the architecture of FIG. 13, comprising a special circuitry (shown as ADC) to obtain sufficient resolution (around 20-bit) with accurate timing of samples, comprising first analog to digital converter ADC1 and a compensation circuit, comprising digital to analog converter DAC1, a summing amplifier, and second analog to digital converter ADC2.

Unfortunately, ADCs with such a resolution are not sufficiently fast. Therefore, a special circuitry shown in FIG. 14 is designed to obtain required resolution (around 20 bit) with accurate timing. The modulated sine wave response signals from an analog multiplexer MUX have been amplified to the 0.5V amplitude (1V peak-to-peak value). The bio-modulation from heart beating, blood circulation and breathing is typically about 1%, but frequently only 0.01% of the amplitude of its carrier, that is from 100 μV to 10 mV peak-to-peak.

First, the response signal is sampled and digitized in a ADC1. Then the digital samples are inverted and converted back to analog signals using a digital-to-analog converter DAC1. In a summing amplifier, the output of the ADC1 is subtracted from the response signal and the result is amplified 128 times (corresponds to 7 bits). After that the output of the amplifier will be digitized by ADC2. This way the constant values of a large carrier are compensated, useful modulation is amplified and 7 additional bits at the conversion rate of a 12-bit ADC are received.

Figure 16:
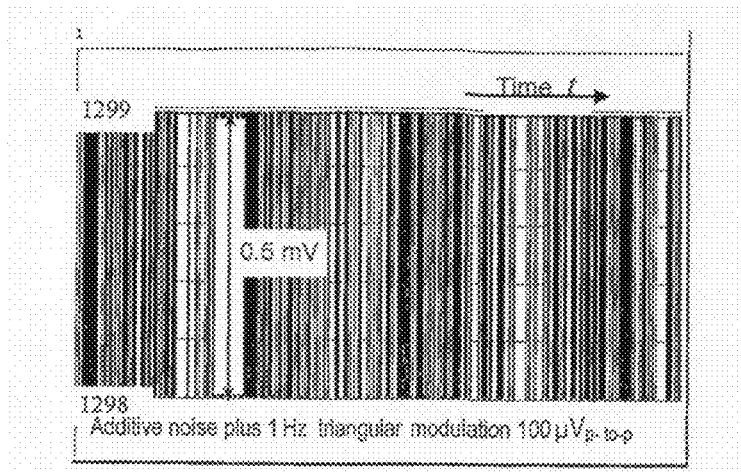
FIG. 16 depicts the output code of the ADC1 of FIG. 14 to a signal with 0.01% triangular amplitude modulation (100 microvolt peak-to-peak value), where $Re^+$ values of the response signal are sampled.
Figure 17:
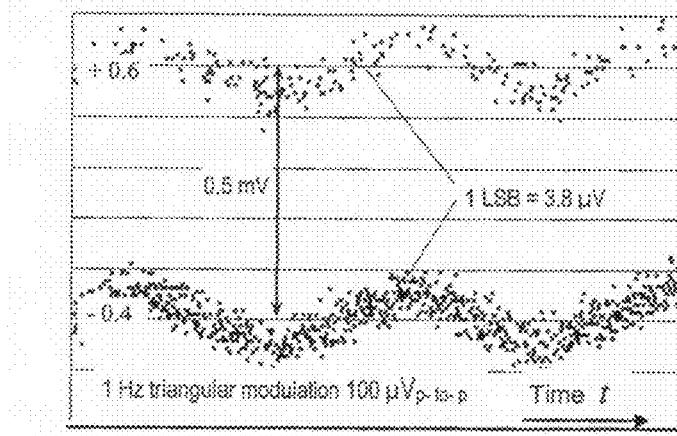
FIG. 17 depicts the output code of ADC 2 in FIG. 14 corresponds to the same signal as in FIG. 16.
Figure 18:
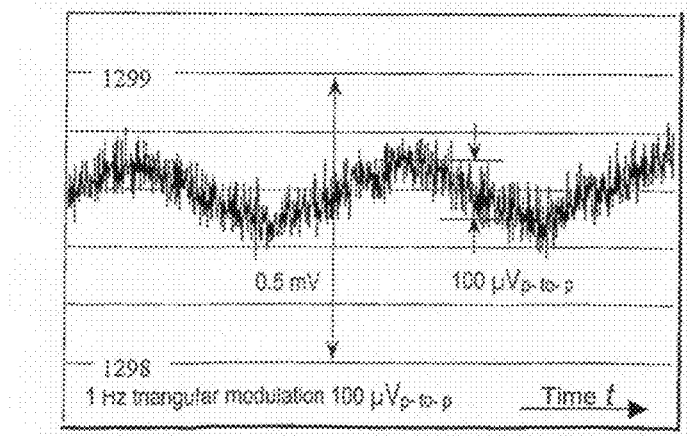
FIG. 18 depicts the digital signal, stored in FPGA, and corresponding to the same signal as in FIGS. 16 and 17.

The results of the ADC of FIG. 14 are depicted in FIGS. 16 to 18. In FIG. 16, there are given variations of the output code of the converter ADC1, when Re+ values of the response signal (see FIG. 4) are sampled. A 0.01% triangular amplitude modulation (1 Hz, 100 μV peak-to peak value) of an half full scale 1V peak-to-peak carrier has been used for testing. The modulation is several times smaller than 1 LSB (488 μV), but due to a significant additive noise, the output changes almost randomly between two discrete levels (codes 1298 and 1299). There is almost no possibility to extract any useful information from this code.

The output code of ADC1 is converted to analog signal in DAC1 and subtracted from the input voltage. The difference is gained by the summing amplifier, e.g. 128 times, and is digitized in ADC2. As a result, the effective resolution is now 3.8 μV instead of initial 488 μV.

The stored digital signal based on raw data from ADC1 and ADC2 shows that even a simple signal processing as averaging or low pass filtering can give clearly informative results.

For example, in test arrangement, the signals were digitized with a 12-bit analog-to-digital converter AD9236 from Analog Devices, having a 2V differential input range and 80 MSPS sampling rate (see ADC1 and ADC2 in FIG. 14). The value of the least significant bit (LSB) of these ADCs is 488 μV. Compensation voltage was generated with the 12-bit high speed digital-to-analog converter (DAC1) AD9762 from Analog Devices, having a 125 MSPS sampling rate The summing amplifier with gain control was constructed on the basis of high performance differential amplifier AD8139 from Analog Devices, and high-speed programmable-gain amplifier THS7002 from Texas Instruments. Test setup parameters included 8 excitation sources, and 8 signals to measure, typical frequency range of interest being 30 kHz to 100 kHz. Isolation barrier (see FIG. 14) comprised four-channel 5 kV isolators ADuM2402 from Analog Devices.

Figure 15:
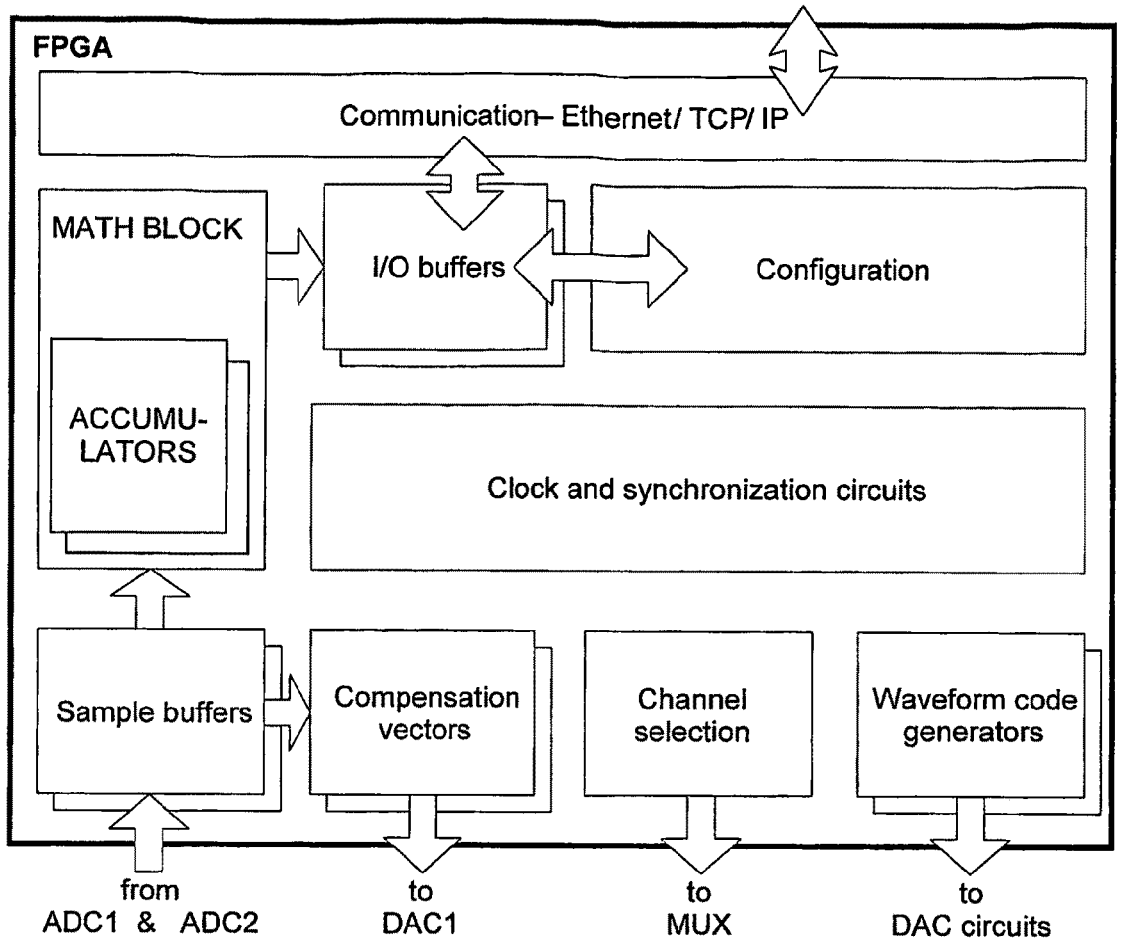
FIG. 15 depicts a functional block diagram of a field programmable gate array (FPGA), designed to implement the architecture of FIG. 13 and handling input channel selection, sampling pulse generation, preamplifier gain control, compensation voltage code generation (see FIG. 14), reading of samples from digital quanticiers (ADCs), performing math functions, generating excitation signal codes, and communication.

The bioimpedance measurement unit (BMU) as shown in FIG. 14 is implemented using proprietary Field Programmable Gate Array (FPGA) Spartan™-3 from Xilinx. The FPGA handles input channel input channel selection, sampling pulse generation, preamplifier gain control, compensation voltage code generation (see FIG. 15), reading of samples from digital quanticiers (ADCs), performing math functions, generating excitation signal codes, and communication.

The analyser in FIG. 13 has to find the eight bioimpedances of different frequency/tissue channels on the basis of every measured summary response voltage. Separation of the offsets is of interest too.

In order to make the bioimpedances of different tissue channels (between excitation and measurement electrodes) comparable at several frequencies (L levels), the frequencies of the excitations sent to different electrodes must be sufficiently close to the others at every level l=1, 2, . . . L, where L=8/K for eight frequencies, where K is the number of excitation electrodes. This requirement was presented in the form:

$$(f_{k+1,l} - f_{k,l})/f_{k,l} \leq 0.1 \text{ for all } l \text{ and } k \in \{1, \ldots, K-1\}$$

It is desired to obtain the bioimpedance values for all the tissue/frequency channels with a frequency $f_R$.

Last, but not least: signal processing must guarantee sufficient noise suppression for further analysis of the useful bio-modulation signal (variation of the bioimpedance due to the heartbeats and breathing), which is usually from a fraction up to some percent of the whole bioimpedance.

In the analyser the excitation frequencies $f_p$ (p=1 to 8) and also the sampling frequencies $f_s$ are chosen to be integer multiples of the frequency $f_R$. As in the developed analyser the whole signal path from the generation of the set of excitation signals to the A/D conversion procedure and data analysis is synchronous by design, optimized signal processing methods can be applied.

The frequency components of the entire test signal are designed to meet the endpoint discontinuity requirements and are therefore well suited for direct discrete Fourier analysis without applying preceding windowing procedure. The ratios of the sampling and excitation frequencies are chosen to minimize the analysis-errors caused by mutual interference of the responses.

The complex values of the bioimpedances Z can be found processing the responses from the measurement electrodes in two basic ways, which both use undersampling (aliasing) and sparsity of the excitation/response spectrum.

First solution is based on well-known discrete Fourier transform (DFT). Arbitrary desired Z is found in result of a direct DFT of the response.

It is evident, that in such a case the choice of excitation frequencies is restricted: their ratios must have properly chosen values. A more restricted choice of the excitation and sampling frequencies (their ratios) allows us to find $Z(f_p)$ for all $f_p$ as Fourier coefficients of fixed (or even consecutive) numbers.

The DFT is performed so that only the (nonzero) coefficients for the used excitation frequencies are computed. In case of single-point DFT the analysis frequency always matches the input frequency and only the energy at one frequency bin of the DFT spectrum is looked. As a result, the amount of computations is reduced. Analogous approach is used in the commercially available impedance converter network analyser AD5933.

The second solution is based on digital synchronous detection (DSD), where real and imaginary components $R(f_p)$ and $X(f_p)$ of the complex impedance $\dot{Z}$ are found.

The signal system and computation algorithm of this solution use a single sampling frequency.

In the signal system with P sinusoidal excitation signals of different frequencies the excitation frequencies must be $f_p = J_p \cdot 2^{p-1} \cdot f_R$, p=1, 2, . . . , P, where $f_R$ is the repetition rate of the excitation and measurement cycle (the frequency of a sum of P sinusoidal excitations and also of responses) and the odd integers $J_p$ enable to form a set of excitation frequencies, which suit for the measurement task and for formation of excitation signals; the sampling frequency must be $f_S = 2^{P+1} \cdot f_R$ ($N_P = 4 \cdot 2^{P-1} = 2^{P+1}$ samples per measurement cycle/interval $T_R = 1/f_R$), and zero values of excitations match with sampling instants.

Example 1 where, due to $f_R$=1 Hz, the sampling frequency $f_S = N_P$, and frequencies of P sinusoidal excitations $f_p$ (p=1, 2, . . . , P) are found in Hz.

| | p | | | | | | | |
|---|---|---|---|---|---|---|---|---|
| | 1 | 2 | 3 | 4 | 5 | 6 | 7 | P = 8 |
| $2^{P-1}$ | 1 | 2 | 4 | 8 | 16 | 32 | 64 | 128 |
| $4 \cdot 2^{P-1}$ | 4 | 8 | 16 | 32 | 64 | 128 | 256 | $N_P$ = 512 |
| $J_p$ | 11 | 5 | 25 | 13 | 63 | 33 | 157 | 79 |
| $f_p = J_p \cdot 2^{P-1}$ | 11 | 10 | 100 | 104 | 1008 | 1056 | 10048 | 10112 |

Example 2 where, due to $f_R$=1 Hz, the sampling frequency $f_S$=$N_P$, and frequencies of P sinusoidal excitations $f_p$ (p=1, 2, . . . , P) are found in Hz.

| | p | | | | | | | |
|---|---|---|---|---|---|---|---|---|
| | 1 | 2 | 3 | 4 | 5 | 6 | 7 | P = 8 |
| $2^{P-1}$ | 1 | 2 | 4 | 8 | 16 | 32 | 64 | 128 |
| $4 \cdot 2^{P-1}$ | 4 | 8 | 16 | 32 | 64 | 128 | 256 | $N_P$ = 512 |
| $J_p$ | 3 | 5 | 25 | 125 | 625 | 1 | 5 | 25 |
| $f_p = J_p \cdot 2^{P-1}$ | 3 | 10 | 100 | 1000 | 10000 | 32 | 320 | 3200 |

If such signal system is used, then real and imaginary parts of the bio-impedance $\dot{Z}(f_p)=R(f_p)+jX(f_p)$, by which the voltage response component $v_p$ of the frequency $f_p$ has been modulated, can be found for every measurement cycle (of the length $T_R=1/f_R$) performing the next steps:

1) Summation of all the response's $2^{P+1}$ samples v(n), n=1, 2, . . . , $2^{P+1}$ over the measurement cycle (the interval $T_R$) according to $$S_{Rep} = \sum_{k=1}^{2^{P+1}} w_{Rep}(n) \cdot v(n) \text{ and } S_{Imp} = \sum_{k=1}^{2^{P+1}} w_{Imp}(n) \cdot v(n)$$

using the earlier computed weights (−1, 0, +1 patterns)

$$w_{Rep}(n)=(\text{mod}(n, 2^{P+1-p}) \neq 0) \cdot \text{sign}(\sin(n \cdot J_p \cdot \pi/2^{P+1-p}))$$

$$w_{Imp}(n)=(\text{mod}(n, 2^{P+1-p}) \neq 2^{P-p}) \cdot \text{sign}(\cos(n \cdot J_p \cdot \pi/2^{P+1-p}))$$

The DC component (offset) of the response v can be found using constant weights w(n)=1.

2) Real and imaginary parts of the impedance $\dot{Z}(f_p)$ are found according to $$R(f_p)=S_{Rep} \cdot C_p/I_p \text{ and } X(f_p)=S_{Imp} \cdot C_p/I_p$$

where $I_p$ is a magnitude of the p-th excitation current and the coefficient $$C_p = \left(1 + 2\sum_{q=1}^{2^{P-p}} \cos(q\pi/2^{P+1-q})\right) / 2^P.$$

3) Finally, the magnitude (modulus) and phase of $\dot{Z}(f_p)$ are computed:

$$M(f_p)=|\dot{Z}(f_p)|=\sqrt{(R(f_p))^2+(X(f_p))^2},$$

$$\Phi(f_p)=\arctan(X(f_p)/R(f_p)).$$

The results can be found simultaneously for response's all P components.

Summation of the samples can be performed currently in the measurement cycle (2P additions per response in a sampling interval).

The test results of the prototyped solution were the following:

1) Signal processing capability of the used single digital signal processor (DSP) allows to use in case of 1, 2 and 4 measurement electrodes (1, 2, and 4 multiplexed responses) sampling frequencies up to 800, 400 and 200 kHz correspondingly.

2) Even at these highest possible sampling frequencies the noise suppression achieved by means of the discrete Fourier transformation is not sufficient. The noise masked the small (from fraction up to some percent) modulations caused by the varying bioimpedance. Therefore, before the analog to digital converters, first order analog low-pass filters are used for conditioning the measurement signals and also a digital compensation of the analog filter's frequency response. In this way a sufficiently low noise level was achieved at the output.

3) As a result 0.1% modulation of the 100-ohm base impedance has been clearly distinguished.

In order to compare noise suppression capabilities of the direct discrete Fourier transform and the numerical synchronous detection, we simulated analysis of an eight component test signal with added offset and Gaussian white noise. Results of processing of the test signal, which consisted of sinusoidal components of the frequencies 1, 2, 4, . . . , 128 kHz, at the sampling frequency 512 kHz showed that the mentioned methods both resulted the same noise level and highly correlated noise for every identified sinusoidal component (its parameters: amplitude, phase, real and imaginary parts). Thus, the considered approaches are equivalent in this aspect in this particular case.

The digital synchronous detection (DSD) based approach needs less computation than the DFT based approach. It is important that DSD enables to obtain much more easily the desired results at every sample and (applying additional averaging methods) also the averaged results with lower noise level.

The DSD based approach can be based on use of several sampling frequencies, simultaneous or sequential application of which leads to non-uniform sampling (see FIGS. 7, 8, 10, 12). This approach can be easily applied in a system with M simultaneously working SISO (single input-single output) tissue impedance measurement channels and eliminates interference between these channels. It suits also for alternating (cyclic) measurement of responses to the excitations from M inputs at every output. Also a new hardware solution for a MIMO measurement system (for simultaneous measurement of all these M responses at every measurement electrode), which should be applicable in a low-power ASIC (in implantable measurement systems), is suggested.

Although this invention is described with respect to a set of aspects and embodiments, modifications thereto will be apparent to those skilled in the art. The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

The invention claimed is:

1. Method for multichannel multifrequency analysis of an object, comprising:
   generating a set of excitation signals wherein all excitation signals are periodic signals with preselected frequencies;
   applying said set of excitation signals simultaneously to the object;
   receiving from the object, in response to said set of excitation signals, a response signal corresponding to said set of excitation signals, modulated by the object's properties, said response signal comprising a set of components with different frequencies;
   calculating a set of phase-related sampling instances based on said set of excitation signals, for each frequency of interest and for at least one predetermined observation time slot;
   demodulating said response signal to separate the response to each excitation signal by quantizing and processing of said response signal at each sampling instances of said set of sampling instances, wherein said quantizing is performed for each frequency of interest of said response signal in predetermined mode; and
   obtaining a set of main frequency and time tagged estimates, each of said estimates comprising a plurality of sub-estimates, said sub-estimates representing a signal value, for said observation time slot, wherein the length of said observation time slot is selected so that it contains integer numbers of periods of each excitation signal of said set of excitation signals, wherein each of said estimates are sorted separately so the estimates at each frequency of interest are obtained while impacts of other estimates are cancelled out.

2. A method as in claim 1, wherein said response signal is sampled with predetermined sampling pattern within said observation time slot.

3. A method as in claim 2, wherein said response signal is sampled uniformly within said observation time slot.

4. A method as in claim 2, wherein undersampling is applied to demodulate at least one of said components of said response signal.

5. A method as in claim 2, wherein separating measurement channels in time domain is performed by uniformly sampling said response signal for one frequency of interest for every measurement channel in one observation time slot and for each additional frequency of interest for every measurement channel in corresponding additional observation time slot.

6. A method as in claim 2, wherein separating measurement channels is performed by non-uniformly sampling said response signal for each frequency of interest for one measurement channel in first observation time slot and for each frequency of interest for each additional measurement channel in corresponding additional observation time slot.

7. A method as in claim 6, wherein said response signal is quantized more than once at predetermined sampling rate for at least one sampling instance of said set of sampling instances.

8. A method as in claim 7, wherein said sampling instances are calculated, using said preselected frequencies of each excitation signal of said set of excitation signals and for each frequency of interest.

9. A method as in claim 8, wherein said sampling instances are estimated for said set of excitation signals and for each frequency of interest.

10. A method as in claim 1 wherein at least one frequency of interest of said response signal is compensated by a predetermined signal.

11. A method as in claim 1 wherein at least one frequency of interest of said response signal is compensated by an estimated signal.

12. A method as in claim 1 wherein at least one frequency of interest of said response signal is compensated using analogue compensation.

13. A method as in claim 1 wherein at least one frequency of interest of said response signal is compensated using digital compensation.

14. A method as in claim 1, wherein an inphase sampling is applied for said frequency of interest, wherein obtained inphase samples are used to separate inphase estimates.

15. A method as in claim 1, wherein a quadrature sampling is applied for said frequency of interest, wherein obtained quadrature samples are used to separate quadrature estimates.

16. A method as in claim 1, wherein off the phase sampling is applied for each frequency of interest, whereas obtained off the phase samples are used for extracting an additive signal component removal of an offset, or a common-mode noise by summing cancellation technique.

17. A method as in claim 1, wherein said preselected frequencies $f_p$ of said excitation signals of said set of excitation signals are chosen according to formula $$f_p = J_p * 2^{p-1} * f_R,$$

where $J_p$ is an integer, p is an integer from 1 to P, where P is the number of excitation signals in said set of excitation signal, and $f_R$ is a repetition rate of an excitation and measurement cycle.

* * * * *